(12) United States Patent
Chan (10) Patent No.: US 10,279,347 B2
(45) Date of Patent: May 7, 2019

(54) FLUIDICS MODULE

(71) Applicant: DNA Medicine Institute, Inc., Cambridge, MA (US)

(72) Inventor: Eugene Y. Chan, Boston, MA (US)

(73) Assignee: DNA Medicine Institute, Inc., Cambridge, MA (US)

( * ) Notice: Subject to any disclaimer, the term of this patent is extended or adjusted under 35 U.S.C. 154(b) by 117 days.

(21) Appl. No.: 14/682,044

(22) Filed: Apr. 8, 2015

(65) Prior Publication Data

US 2015/0283544 A1 Oct. 8, 2015

Related U.S. Application Data

(60) Provisional application No. 61/977,063, filed on Apr. 8, 2014.

(51) Int. Cl.
| | |
|---|---|
| *G01N 1/10* | (2006.01) |
| *B01L 3/00* | (2006.01) |
| *G01N 11/00* | (2006.01) |
| *G01N 35/10* | (2006.01) |
| *G01N 35/00* | (2006.01) |

(52) U.S. Cl.
CPC ............ *B01L 3/50273* (2013.01); *G01N 1/10* (2013.01); *G01N 11/00* (2013.01); *G01N 35/1097* (2013.01); *B01L 3/502715* (2013.01); *B01L 2200/025* (2013.01); *B01L 2300/14* (2013.01); *B01L 2400/0605* (2013.01); *B01L 2400/0666* (2013.01); *G01N 2035/00237* (2013.01)

(58) Field of Classification Search
None
See application file for complete search history.

(56) References Cited

U.S. PATENT DOCUMENTS

| | | | |
|---|---|---|---|
| 2005/0040357 A1* | 2/2005 | Kish, Jr. | F16K 27/003 251/129.17 |
| 2007/0264170 A1* | 11/2007 | Barthe | B01F 13/0059 422/130 |
| 2011/0229961 A1* | 9/2011 | Higashi | C12M 23/16 435/287.1 |
| 2011/0306081 A1* | 12/2011 | Szita | B01L 3/502715 435/29 |
| 2013/0139895 A1* | 6/2013 | Vangbo | B01L 3/502738 137/2 |
| 2015/0268668 A1* | 9/2015 | Nahmias | G05B 15/02 700/282 |

* cited by examiner

*Primary Examiner* — Paul M. West
*Assistant Examiner* — Mark A Shabman
(74) *Attorney, Agent, or Firm* — Danielson Legal LLC (57) ABSTRACT

An integrated fluidics module that reduces mass and volume so that it can readily fit inside a compact biomedical instrument. A fluidics module that integrates discrete components (e.g., pump, connectors, tubing, regulator, and valves) reduces mass and volume requirements.

9 Claims, 9 Drawing Sheets

FLUIDICS MODULE

CROSS-REFERENCE TO RELATED APPLICATIONS

The present application claims the benefit of U.S. provisional application No. 61/977,063, filed on Apr. 8, 2014, the entire disclosure of which is incorporated by reference as if set forth in its entirety herein.

FIELD

The invention relates to fluid handling modules, and specifically to fluid handling modules for a biomedical instrument.

BACKGROUND

Conventional fluid handling for a biomedical instrument uses pumps, vessels, valves, regulators, connectors, tubing, and other components. These conventionally exist as discrete items in an instrument, so that a larger mass and volume is required.

For a compact biomedical instrument, it is highly desired that the fluid handling system be compact and miniaturized. Component selection should be judicious to minimize mass, volume, and power. In this manner, the fluidics module should encompass as many functions as possible to ensure maximal capability for the smallest footprint.

Having discrete components is an impediment to the development of compact biomedical instrumentation. Groups developing compact biomedical instrumentation have previously attempted to integrate a subset of these components. In these partially integrated approaches, the fluidics are still bulky and exist in large part as discrete components.

Microfluidics is an approach for removing the requirement for having significant amounts of tubing. While this is the case, microfluidics typically does not address mechanical components such as pressure regulators, solenoid valves, check valves, and pumps. These approaches typically still require conventional mechanical fluidic components that remain discrete.

While microfluidic integration is important to the field, generally, the greater the level of integration, the more complex and challenging the manufacturing. Furthermore, microfluidics is not as robust when it comes to areas where there are conventional mechanical components, such as pressure regulation and pumping.

In tight of the foregoing, it is desirable to have an improved fluidic manifold to reduce mass, volume, and power required.

SUMMARY

Embodiments of the invention concern a fluidics module that is appropriate for a small benchtop biomedical analyzer. The invention utilizes a judicious selection of off-the-shelf components with a microfluidics manifold. This approach minimizes manufacturing cost and increases robustness while maintaining the advantages of small mass and volume.

In one aspect, embodiments of the present invention relate to a fluid handling system. The fluid handling system includes a microfluidics manifold and at least one of a connector and a mating area integrated into the manifold to facilitate the connection of a discrete component to the manifold.

In one embodiment, the system further comprises a discrete component connected to the manifold. The discrete component may be selected from the group consisting of a miniature valve, a pump, a pressure regulator, a tubing connector, and an air connector.

In one embodiment, the microfluidics manifold includes a three-dimensional spatial network of microfluidic channels. In one embodiment, the system includes a mating area and the mating area is selected from the group consisting of a threaded recess, an inlet, an outlet, a threaded hole, and a mounting hole. In one embodiment, the mating area is one of an inlet and an outlet, and the system further comprises screw holes for connecting the discrete component to the manifold.

In one embodiment, the system comprises a connector selected from the group consisting of a screw and a gasket. In one embodiment, the system comprises a bypassable flow restrictor connected to the microfluidics manifold. In one embodiment, the system further includes at least one check valve connected to the microfluidics manifold.

In another aspect, embodiments of the present invention relate to a method for conducting a fluid analysis utilizing a microfluidics manifold connected to a sample source. The method includes providing pressurized air to the manifold; directing, via the manifold, the pressurized air to at least one vial connected to the manifold; and receiving materials from the at least one pressurized vial via a valve mounted on the manifold, wherein the microfluidics manifold compresses a three-dimensional spatial network of microfluidic channels.

In one embodiment, the pressurized air provided to the manifold is received at a regulator. In one embodiment, the method further includes connecting at least one vial to the manifold. In one embodiment, the method further includes providing a pressurized cleaning fluid to the manifold.

In yet another aspect, embodiments of the present invention relate to a fluid handling system. The fluid handling system includes a microfluidics manifold; a discrete pump connected to the manifold, providing pressurized air to the manifold; and at least one vial connected to the manifold, wherein the microfluidics manifold comprises a three-dimensional spatial network of microfluidic channels.

In one embodiment, the fluid handling system further includes a regulator connected to the manifold, the regulator receiving pressurized air from the pump and providing a uniform air flow with steady pressure. In one embodiment, the at least one vial is connected to the manifold by a valve. The valve may be, e.g., a solenoid valve or a latching valve. In one embodiment, the system comprises three vials connected to the manifold: a sample vial, a cleaning vial, and a vial for waste. In one embodiment, the system further includes a bypassable flow restrictor connected to the manifold. In one embodiment, the system further includes at least one check valve connected to the manifold.

The foregoing and other features and advantages of the present invention will be made more apparent from the descriptions, drawings, and claims that follow. One of ordinary skill in the art, based on this disclosure, would understand that other aspects and advantages of the present invention exist.

BRIEF DESCRIPTION OF DRAWINGS

In the drawings, like reference characters generally refer to corresponding parts throughout the different views. The drawings are not necessarily to scale, emphasis instead being placed on the principles and concepts of operation.

DETAILED DESCRIPTION

In embodiments of the present invention, tubing and connectors are minimized and the majority of the fluidic components are somehow attached to a fluidics manifold, thus minimizing fluidic connections or tubing length. In one embodiment, the fluidics module utilizes microfluidic means of removing the requirement for significant networks of tubing, Mechanical components, such as off-the-shelf pumps and regulators, can be directly mounted to the manifold to eliminate or minimize connections between the components. Furthermore, judicious use of existing mechanical components such as valves and regulators allows for ease of manufacturing and robustness while maintaining a small footprint.

In one embodiment, the core of the fluidics module is a microfluidics manifold that has a 3D spatial network of microfluidic channels. This 3D spatial arrangement minimizes tubing and interconnects. The advantage of the 3D network is that junctions, intersections, and tubing management are contained within the manifold. The use of this type of manifold increases the level of tubing organization, utilizes a single manifold, and his into a compact space. The fluidics manifold has various connectors and mating areas for conventional mechanical components. There is a threaded recess for a pressure regulator. There are inlets and outlets for low power valves and also connecting screw holes that allow the valves to the mounted. There are threaded screw holes for leak-proof tubing connectors that lead to other parts of the instrument, including sample and waste vials. There is a mounting hole for the diaphragm pump. The shape of the module is compact and follows the form of the biomedical instrument. There are also screw mounting holes for manifold to the instrument.

Mating of components to the module is facile. The manifold has various threaded holes or threaded inserts that accept mechanical components. For instance, the valves are secured by screws. Gaskets on the valves mate to the manifold. The screws press the valve against the surface of the manifold. The holes on the valve mate with those on the manifold to allow passage of fluid from the inlet to the outlet of the valve. A series of valves are located on the manifold. The pressure regulator is a screw-in type pressure regulator. An O-ring type seal is formed between the pressure regulator and the manifold. Tubing connectors are also screw-in type to ensure robust seals. Air connectors take in pump air or deliver the regulated and unregulated air to pressure sensors on an electronics board. The system allows for priming, cleaning, and sample analysis modes.

Other parts of the fluidic system include the sample vials, flow cell, sample loader, and burp line for a flow cytometer instrument. The sample vials contain sheath fluid, cleaning fluid, and waste. The flow cell assembly has four ports: sample inlet, sheath, and burp port, and waste. Tubing connects the fluidics module to the sample loader, which in turn is connected to the inlet of the flow cell. Pressure and fluid attached to the burp line allows for bubble removal and priming. A series of check valves in the system prevent backwards movement of fluid. Overall, the greater fluidic system relies on the simplicity of the fluidics module to manage its interactions. The fluidics module is thus the hub of the fluidics system.

The invention therefore bypasses the limitations of conventional technologies in that it provides fluidic integration and manufacturability. This is in contrast to existing microfluidic integration approaches which have high manufacturing complexity. This invention's hybrid approach allows for utilization of off-the-shelf valves, regulators, connectors, and pumps to maximize simplicity of the fluidics. The end result is a compact fluidics module and system appropriate for a commercial, compact biomedical analyzer.

In one embodiment, the fluidics module is fabricated by 3D printing using a clear, translucent plastic such Watershed XC 11122, which is translucent and water resistant. The screw holes are manually tapped to allow for tubing connectors (IDEX, Mass.). Miniature valves are utilized for actuation (The Lee Company, Conn.). The pressure regulator and pump are commercial off-the-shelf components. The pump is a conventional diaphragm air pump that operates between 0-15 psi. 1/16" OD, 0.020" ID FEB tubing is utilized to connect the vials to air and to the ports on the manifold. Flexible tygon tubing is utilized to connect the air pump to the manifold and the pressure sensors to the manifold. Flow restrictor tubing is 1/16" OD, but with smaller ID, as low as 0.003" ID. Commercially-available check valves are utilized in the system to prevent backflow.

The manifold receives air from the air pump. Once the air is in the manifold, the unregulated air is directed towards a pressure sensor and to the regulator. The regulator stabilizes the air flow to produce a uniform and steady pressure output. The regulated air is also measured by a pressure sensor. Regulated air is directed towards two fluid vials, a sheath and a cleaner vial. This pressurizes the vials. Flow from these vials is controlled by solenoid valves that are located on the manifold. These valves are directly mounted onto the manifold assembly. Opening of various valves allow for movement of the sample and flow focusing in the system. The sample loader, sheath, and waste need to be opened in order for the sample to be flow focused in a cytometer biomedical instrument. The flow restrictor creates a differential flow rate between the sample and the sheath, allowing the sample to be focused down to a small, thin stream, suitable for cytometry measurements. The channels in the manifold are 0.020" wide. The flow restrictor can be bypassed with the right combination of the valving, allowing the sample to move to the flow cell in a much more rapid manner. The sample line can be cleaned utilizing the cleaning fluid and appropriate actuation of the right sequence of the valves.

The fluidics module is designed for use in a portable cytometer where there is limited volume and thus fluidic integration is paramount. The fluidics module is attached to a flow cell assembly that has a sample input, burp line input, sheath fluid input, and a waste port. The sample line is driven by the sheath fluid. The waste goes through the manifold, to a valve, and then to a waste vial. The burp line is directly connected to the flow cell assembly. The burp line is utilized to clear any bubbles from the system. The sample loader allows a small sample (5-10 µL) to be loaded in-line with the rest of the system. Various check valves are strategically located throughout the fluidics system so that flushing through the burp lines allows for high pressure flushing. Check valves can prevent backflow at higher pressures than solenoid valves. Overall, the fluidics module is at the core of the larger fluidics system.

Figure 1:
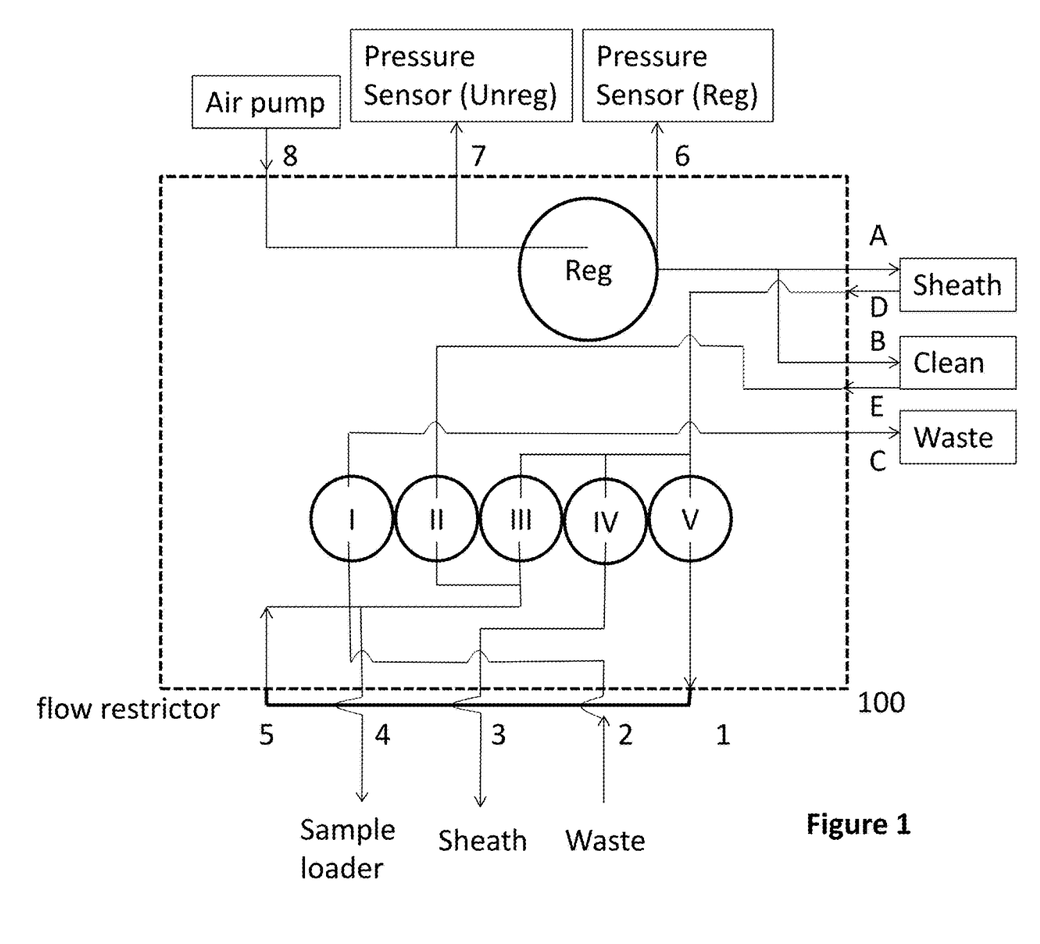
FIG. 1 shows a block diagram schematic of one exemplary embodiment of the fluidics system in accord with the present invention.

FIG. 1 shows a block diagram schematic of one exemplary embodiment of the fluidics system. The dotted line represents the manifold 100. Five valves are labeled I-V. Air ports are labeled 6-8. Connector ports are labeled 1-5. "Reg" stands for regulator; "unreg" stands for unregulated air. A-E represents the connections to the vials. One of ordinary skill would understand that the number of ports and their configuration will necessarily vary from embodiment to embodiment, and thus this example is in no way intended to limit the scope of the invention.

Figure 2:
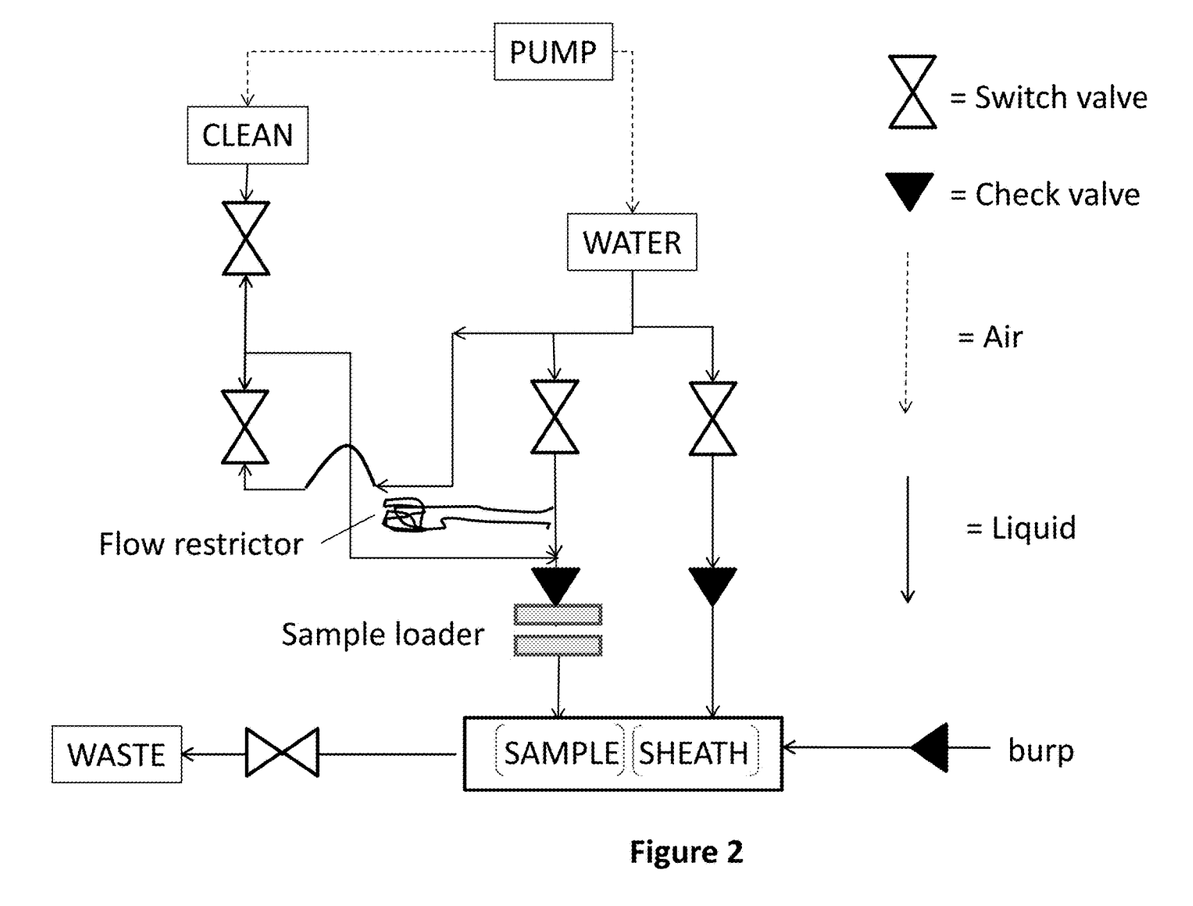
FIG. 2 shows the overall system valving schematic for the embodiment of FIG. 1 with flow restrictors, check valves, and solenoid valves.
Figure 3:
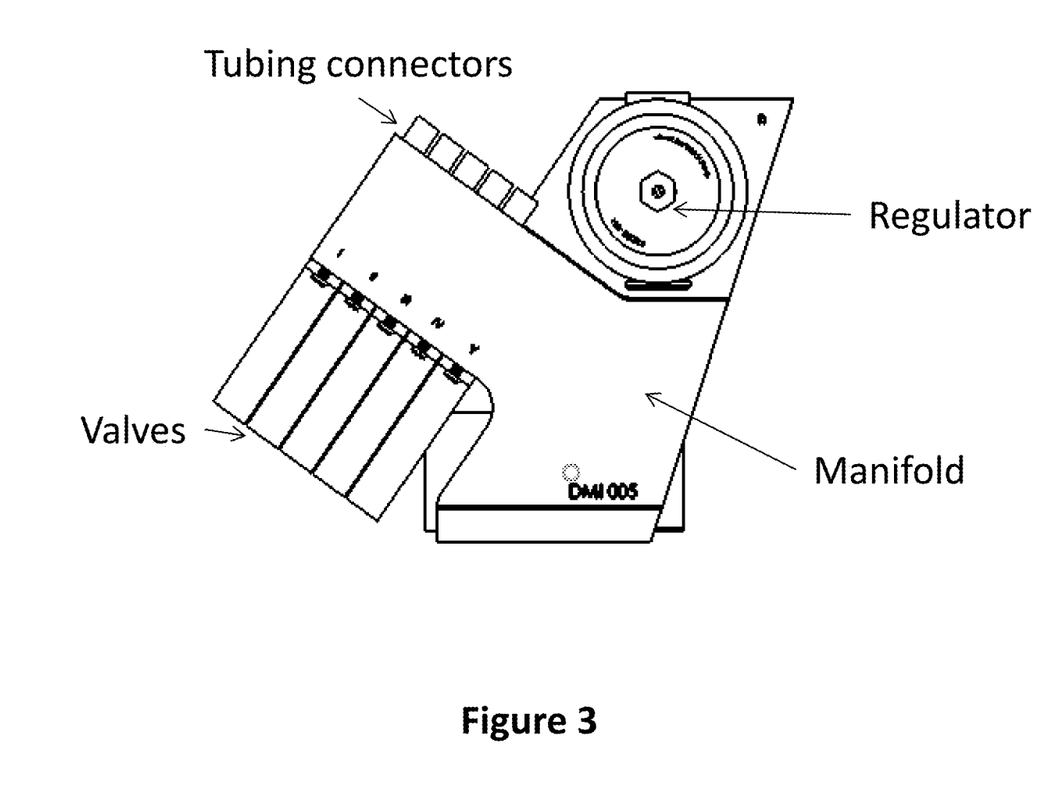
FIG. 3 shows the front view of one non-limiting embodiment of a fluidics module comprising the manifold, valves, tubing connectors, and regulator.

FIG. 2 shows the overall system valving schematic for the embodiment of FIG. 1 with flow restrictors, check valves, and solenoid valves;

FIG. 3 shows the front view of one non-limiting embodiment of a fluidics module comprising the manifold, valves, tubing connectors, and regulator.

Figure 4:
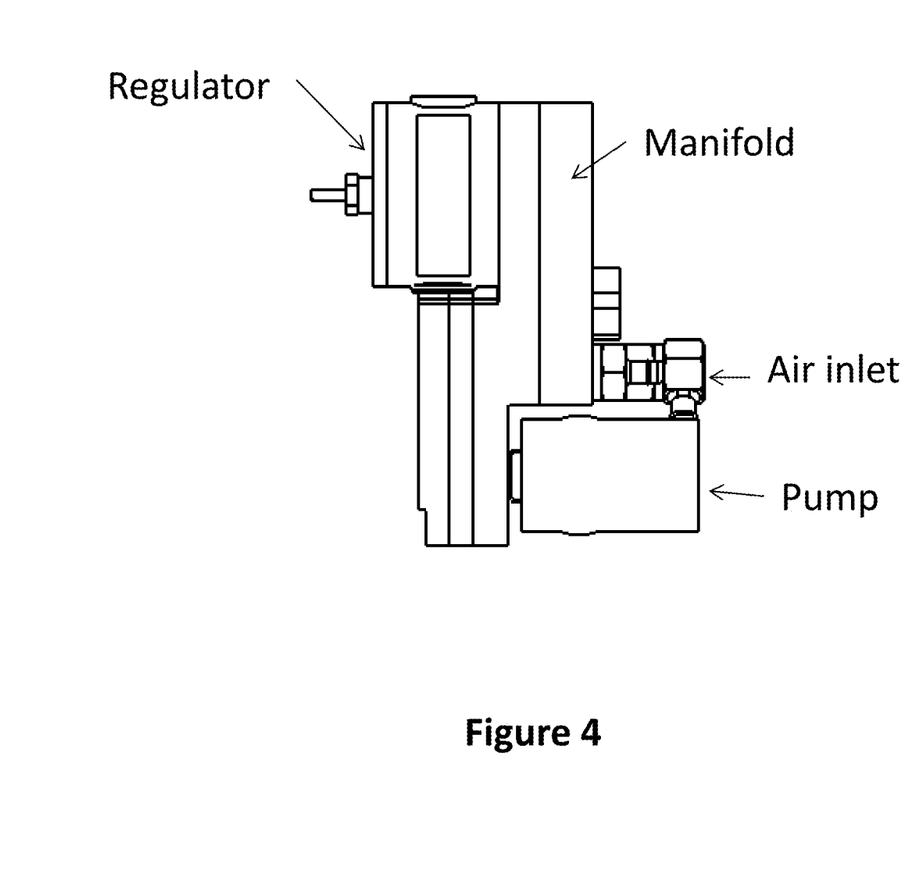
FIG. 4 shows the side view of the exemplary fluidics module of FIG. 3 including the manifold, regulator, air inlet, and pump.

FIG. 4 shows the side view of the exemplary fluidics module of FIG. 3 including the manifold, regulator, air inlet, and pump.

Figure 5:
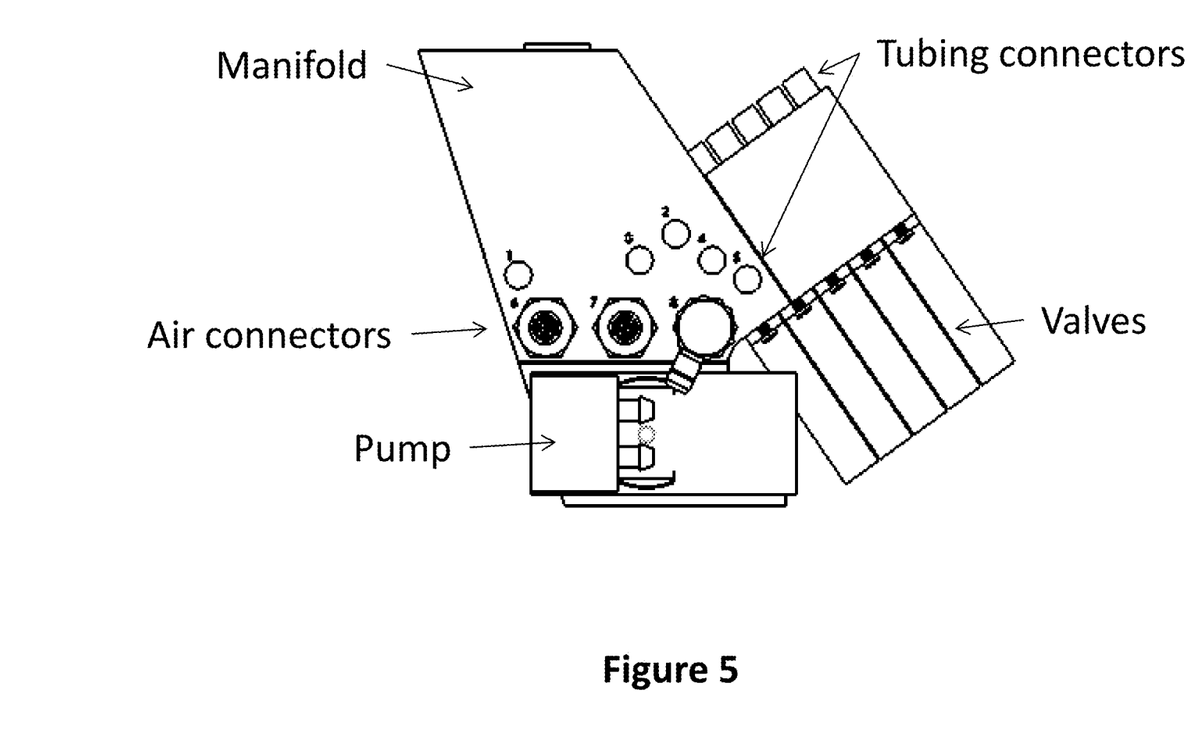
FIG. 5 shows the back view of the exemplary fluidics module of FIG. 3 comprising the manifold, air connectors, pump, tubing connectors, and valves.

FIG. 5 shows the back view of the exemplary fluidics module of FIG. 3 including the manifold, air connectors, pump, tubing connectors, and valves.

Figure 6:
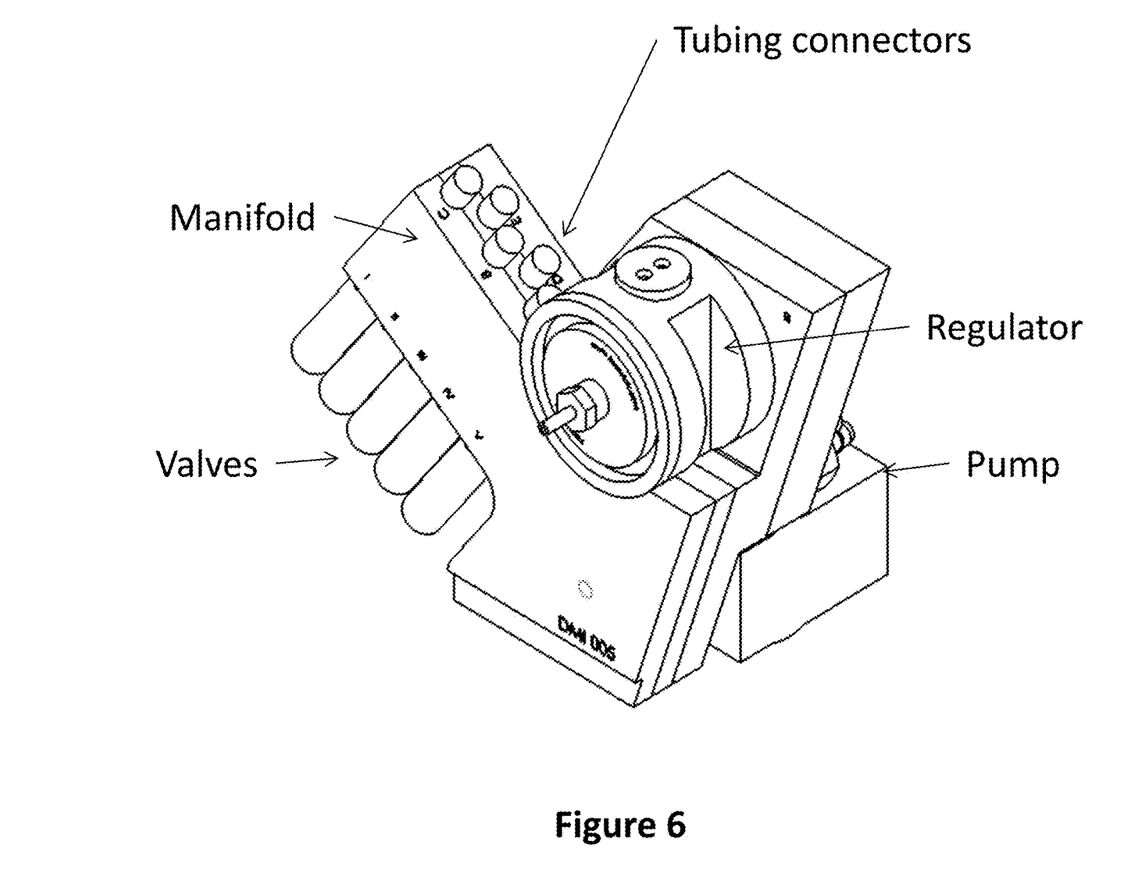
FIG. 6 shows an isometric view of the exemplary fluidics module of FIG. 3 with the manifold, valves, tubing connectors, regulator, and pump.

FIG. 6 shows an isometric view of the exemplary fluidics module of FIG. 3 including the manifold, valves, tubing connectors, regulator, and pump.

Figure 7:
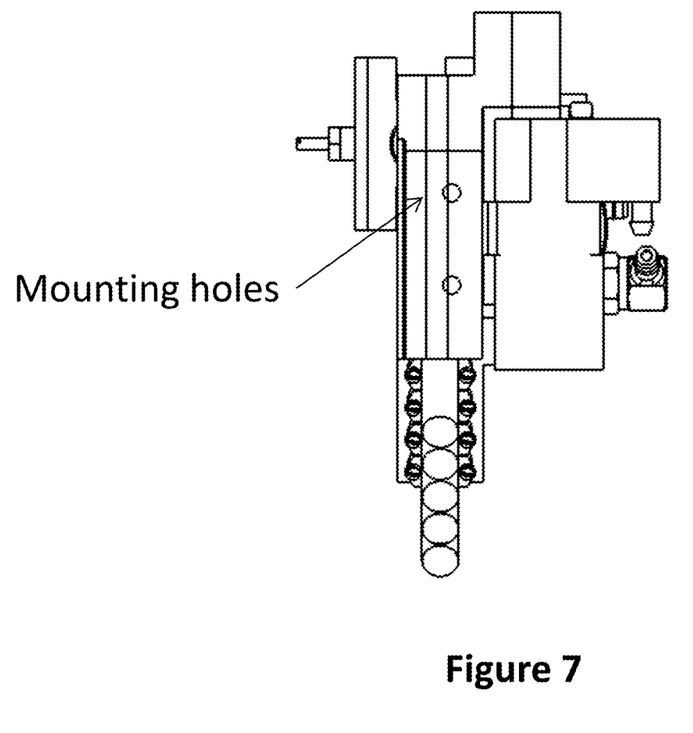
FIG. 7 shows the bottom view of the exemplary fluidics module of FIG. 3 showing mounting holes to the biomedical instrument.

FIG. 7 shows the bottom view of the exemplary fluidics module of FIG. 3 with mounting holes to the biomedical instrument.

Figure 8:
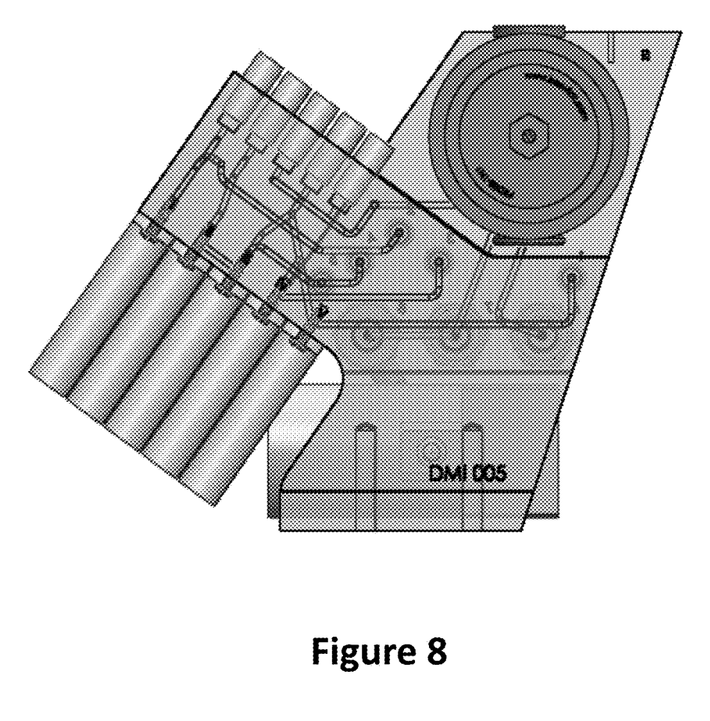
FIG. 8 shows a 3D CAD front view of the exemplary fluidics module of FIG. 3, illustrating the channels within the manifold.

FIG. 8 shows a 3D CAD front view of the exemplary fluidics module of FIG. 3 illustrating the channels within the manifold.

Figure 9:
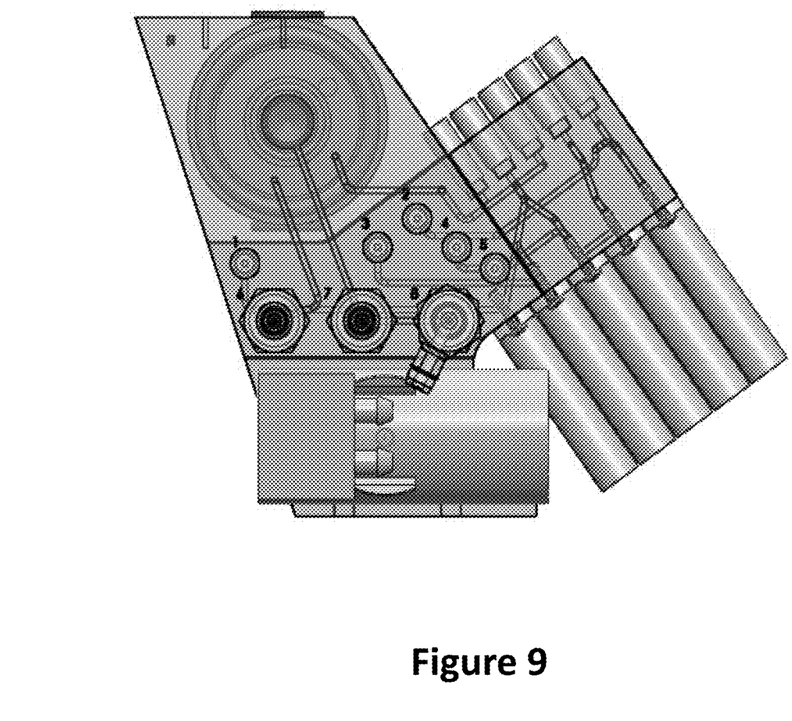
FIG. 9 shows a 3D CAD back view of the exemplary fluidics module of FIG. 3, illustrating the channels within the manifold.

FIG. 9 shows a 3D CAD back view of the exemplary fluidics module of FIG. 3 illustrating the channels within the manifold.

In other embodiments, the shape and size of the fluidics module can vary. Furthermore, the number of valves, regulators, connectors, pumps, vials, and flow restrictors can also vary in type and number. The invention is designed to teach integration of multiple discrete mechanical fluidic components with a 3D network of channels for reducing the overall mass, volume, and power of any fluidic system in a biomedical instrument.

Those skilled in the art will recognize, or be able to ascertain using no more than routine experimentation and/or engineering, many equivalents to the specific embodiments of the invention described herein. The scope of the present invention is not intended to be limited to the above Description, but rather is as set forth in the claims that follow the reference list.

What is claimed is:

1. A fluid handling system comprising:
   a microfluidics manifold;
   a threaded mating area integrated into the manifold to facilitate the connection of a discrete component to the manifold;
   a pressure regulator connected to the manifold and configured to provide a uniform and steady pressure output to a vial; and
   at least one air-pressurized vial connector connected to the manifold, wherein the vial is attached to the air-pressurized vial connector and is configured to receive the uniform and steady pressure output.

2. The system of claim 1 further comprising the discrete component connected to the manifold.

3. The system of claim 2 wherein the discrete component is selected from the group consisting of a miniature valve, a pump, a second pressure regulator, a tubing connector, and an air connector.

4. The system of claim 1 wherein the microfluidics manifold comprises a three-dimensional spatial network of microfluidic channels.

5. The system of claim 1 wherein the mating area is one of an inlet and an outlet, and the system further comprises screw holes for connecting the discrete component to the manifold.

6. The system of claim 1 comprising a connector, wherein the connector is selected from the group consisting of a screw and a gasket.

7. The system of claim 1 further comprising a bypassable flow restrictor connected to the microfluidics manifold.

8. The system of claim 1 further comprising at least one check valve connected to the microfluidics manifold.

9. The system of claim 1 further comprising the discrete component connected to the manifold using a connector threadably inserted into the threaded mating area.

* * * * *